(12) United States Patent
Saito et al.

(10) Patent No.: US 9,683,959 B2
(45) Date of Patent: Jun. 20, 2017

(54) METHOD FOR SETTING TEMPERATURE RISE PROFILE OF SENSOR ELEMENT OF GAS SENSOR

(71) Applicant: NGK INSULATORS, LTD., Nagoya-shi, Aichi (JP)

(72) Inventors: Naoya Saito, Nagoya (JP); Takayuki Sekiya, Nissin (JP); Hiroki Fujita, Kasugai (JP)

(73) Assignee: NGK INSULATORS, LTD., Nagoya (JP)

( * ) Notice: Subject to any disclaimer, the term of this patent is extended or adjusted under 35 U.S.C. 154(b) by 151 days.

(21) Appl. No.: 14/662,399

(22) Filed: Mar. 19, 2015

(65) Prior Publication Data

US 2015/0268192 A1 Sep. 24, 2015

(30) Foreign Application Priority Data

Mar. 24, 2014 (JP) .................. 2014-059986

(51) Int. Cl.
   G01N 27/419 (2006.01)
   G01N 27/406 (2006.01)
   G01N 27/12 (2006.01)
(52) U.S. Cl.
   CPC ....... *G01N 27/419* (2013.01); *G01N 27/4067* (2013.01)
(58) Field of Classification Search
   CPC ............. G01N 27/419; G01N 27/4067; G01N 27/046; G01N 27/123
   See application file for complete search history.

(56) References Cited

U.S. PATENT DOCUMENTS

| 5,763,763 | A  | 6/1998 | Kato et al. |
| 6,921,883 | B2 | 7/2005 | Kato et al. |

FOREIGN PATENT DOCUMENTS

| EP | 1014083 A2 | 6/2000 |
| EP | 1239282 A2 | 9/2002 |
| EP | 1358925 A2 | 11/2003 |
| JP | 9-113484 A | 5/1997 |
| JP | 4344486 B2 | 7/2009 |

OTHER PUBLICATIONS

The Extended European Search Report for the corresponding European patent application No. 15160216.6 issued on Aug. 26, 2015.

*Primary Examiner* — Susan D Leong
(74) *Attorney, Agent, or Firm* — Global IP Counselors, LLP (57) ABSTRACT

A method for setting a temperature rising profile of a sensor element in the activation of a gas sensor is capable of quickly increasing the temperature of the sensor element while reliably preventing or reducing the occurrence of a crack. The method includes Weibull plotting a failure rate that is a cumulative frequency at which a crack occurs as a result of the rapid temperature rising of the sensor element, identifying a temperature-rising-rate upper limit from the plotting results, determining, based on the temperature-rising-rate upper limit, a temperature-rise upper limit curve, and determining, as an appropriate function, a temperature rising profile in a range in which a temperature rising rate at an appropriate temperature does not exceed values on the temperature-rising-rate upper limit curve for the temperature.

20 Claims, 7 Drawing Sheets

METHOD FOR SETTING TEMPERATURE RISE PROFILE OF SENSOR ELEMENT OF GAS SENSOR

BACKGROUND OF THE INVENTION

Field of the Invention

The present invention relates to a method for setting a temperature rising profile to be used to increase the temperature of a sensor element in initiating the use of a gas sensor.

Description of the Background Art

Various gas sensors have been conventionally used to obtain the concentration of a desired gas component of a measurement gas. For example, a NOx sensor including a sensor element formed of an oxygen-ion conductive solid electrolyte such as zirconia ($ZrO_2$) is well known as a device that measures the NOx concentration of a measurement gas such as a combustion gas (for example, see Japanese Patent Application Laid-Open No. 09-113484 (1997) and Japanese Patent No. 4344486).

Japanese Patent Application Laid-Open No. 09-113484 discloses a process of manufacturing a sensor element that forms a gas sensor for obtaining a NOx concentration through introduction of a measurement gas into a space (internal space) provided in the element. In particular, Japanese Patent Application Laid-Open No. 09-113484 discloses a so-called three-chambered sensor element having three internal spaces.

Japanese Patent No. 4344486 discloses the use of, for example, a curve obtained by approximating, to an exponential function (first order lag-time function), the change in the heater resistance value relative to the time passed for increasing the temperature of the sensor element.

In initiating the use of a gas sensor as disclosed in Japanese Patent Application Laid-Open No. 09-113484 and Japanese Patent No. 4344486, the temperature of a sensor element needs to be increased to a predetermined operating temperature by a heater included in the element such that the sensor element can perform measurement, and oxygen needs to be pumped out of an internal space, in which a measuring electrode is included, such that the oxygen concentration in the internal space becomes equal to or lower than a predetermined value at which substantially no oxygen is assumed to be present. The period of time, from a time at which a gas sensor is started to be energized for use to a time at which the gas sensor becomes available, is referred to as a light-off time.

The light-off time is preferably shorter and, to obtain a shorter light-off time, the sensor element is required to be heated to an operating temperature as quickly as possible. However, an excessively high temperature rising rate causes a crack in the sensor element due to a thermal stress acting on the sensor element.

In conventional cases, unfortunately, the following operations have been merely performed: temperature is increased at a constant temperature rising rate at which the occurrence of no crack has been empirically confirmed, or as disclosed in Japanese Patent No. 4344486, feedback control is used in which an increasing rate of heater resistance is reduced every time the measured heater resistance reaches a predetermined value. Such operations are not necessarily optimized from the viewpoints of the prevention or reduction of cracks and the reduction of a light-off time.

SUMMARY OF THE INVENTION

The present invention relates to a method for setting a temperature rising profile for use to increase the temperature of a sensor element formed of an oxygen-ion conductive solid electrolyte in initiating the use of a gas sensor.

In the present invention, a sensor element is included in a gas sensor and includes at least one internal space into which a measurement gas is introduced; an electrochemical pumping cell formed of a measuring electrode provided in one of the at least one internal space, a pump electrode provided in a portion different from the at least one internal space, and the solid electrolyte; and a heater for heating the sensor element. The gas sensor identifies a concentration of a predetermined gas component of the measurement gas based on a pump current through the electrochemical pumping cell. The temperature rising profile indicates a change in an increased temperature set relative to a temperature rising time when the heater increases the temperature of the sensor element in activation of the gas sensor. A method for setting a temperature rising profile for increasing a temperature of a sensor element according to the present invention includes the steps of a) repeating a rapid temperature rising by the heater, for each of a plurality of the sensor elements having a temperature increased to a predetermined temperature for profile setting by the heater, while changing a temperature rising rate until a crack occurs; b) Weibull plotting a failure rate being a cumulative frequency, at which a crack occurs in the plurality of sensor elements in the rapid temperature rising, for the predetermined temperature for profile setting using the temperature rising rate as a distribution parameter; c) identifying, as a temperature-rising-rate upper limit, a temperature rising rate at which a failure rate is 1 ppm from the results of the Weibull plotting in the step b); d) determining, based on the temperature-rising-rate upper limit for a plurality of temperatures for profile setting that include a temperature equal to or higher than an operating temperature of the sensor element and differ from each other, a temperature-rise upper limit curve indicating a change in the temperature-rising-rate upper limit relative to an increased temperature; and e) determining, as an appropriate function, the temperature rising profile in a range in which a temperature rising rate at an appropriate temperature does not exceed values on the temperature-rising-rate upper limit curve for the temperature.

According to the present invention, a temperature rising profile for increasing the temperature of the sensor element in initiating the use of a gas sensor is determined based on the crack occurrence situation when the temperature of the sensor element is rapidly increased, enabling a quick temperature rise of the sensor element while reliably preventing or reducing the occurrence of a crack.

The present invention therefore has an object to provide a method for setting a temperature rising profile capable of allowing a quick temperature rising of a sensor element while reliably preventing or reducing the occurrence of a crack.

DESCRIPTION OF THE PREFERRED EMBODIMENTS

<Outline Configuration of Gas Sensor>

Figure 1:
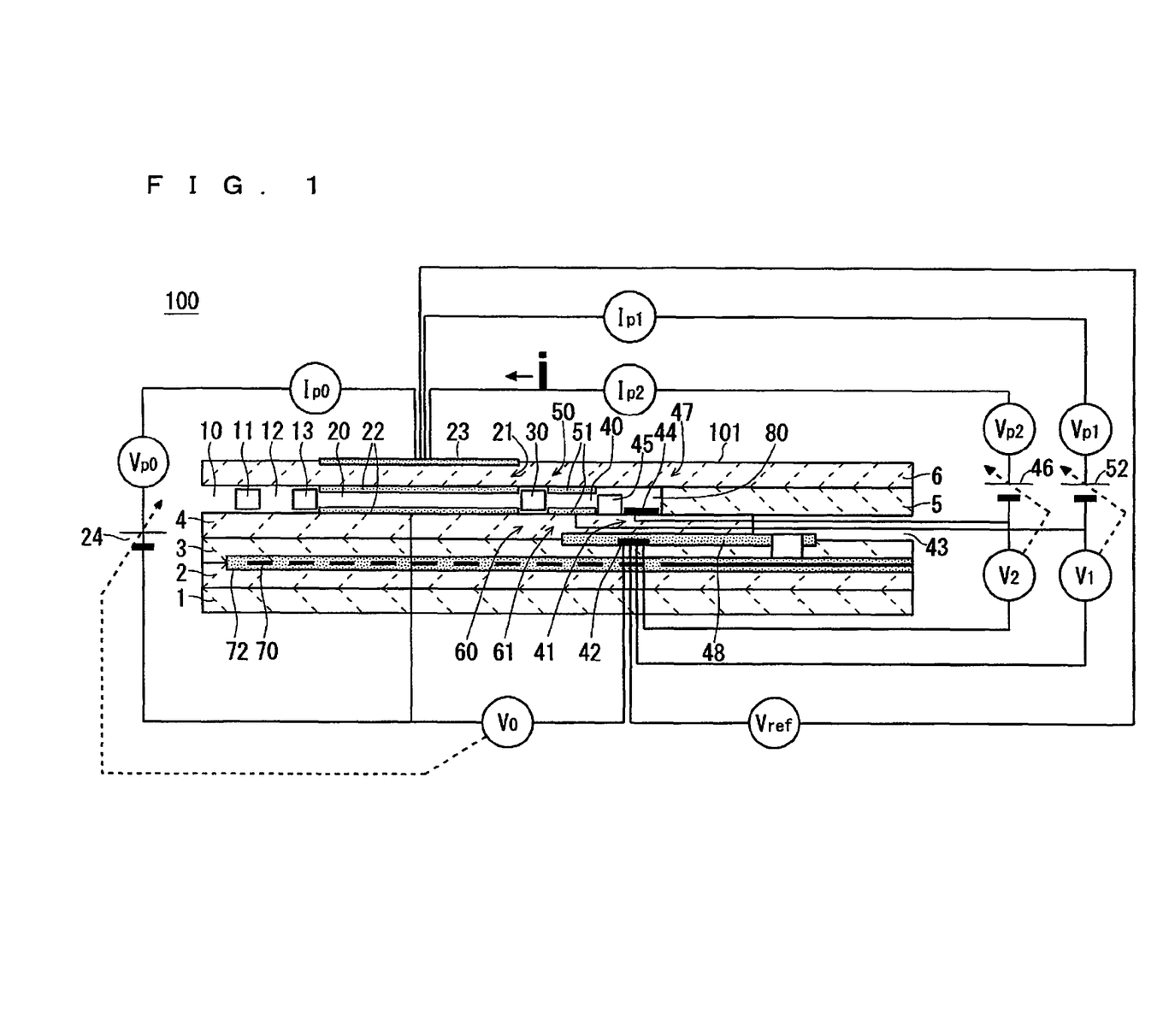
FIG. 1 is a cross-sectional view schematically showing the structure of a gas sensor 100, which is taken along the longitudinal direction of the gas sensor 100.

FIG. 1 is a cross-sectional view schematically showing the structure of a gas sensor 100 according to an embodiment of the present invention, which is taken along the longitudinal direction of the gas sensor 100. The gas sensor 100 according to this embodiment detects a predetermined to-be-measured gas component of a measurement gas and obtains the concentration of the gas component. A sensor element 101 being a main part thereof includes, as a structural material, ceramic mainly composed of zirconia being an oxygen-ion conductive solid electrolyte. The following description is given of an example in which a to-be-measured gas component is a NOx gas.

In outline, the sensor element 101 has the structure in which six layers, namely, a first substrate layer 1, a second substrate layer 2, a third substrate layer 3, a first solid electrolyte layer 4, a spacer layer 5, and a second solid electrolyte layer 6, each formed of an oxygen-ion conductive solid electrolyte, are laminated in the stated order from the bottom side of the sheet of FIG. 1.

Provided between a lower surface of the second solid electrolyte layer 6 and an upper surface of the first solid electrolyte layer 4 on one-end-portion side of the sensor element 101 are a gas inlet 10, a first diffusion control part 11, a first internal space 20, a second diffusion control part 30, a second internal space 40, a third diffusion control part 45, and the third internal space 80. A buffer space 12 and a fourth diffusion control part 13 may be further provided between the first diffusion control part 11 and the first internal space 20. The gas inlet 10, the first diffusion control part 11, the buffer space 12, the fourth diffusion control part 13, the first internal space 20, the second diffusion control part 30, the second internal space 40, the third diffusion control part 45, and the third internal space 80 are adjacently formed so as to be in communication with one another in the stated order. The part extending from the gas inlet 10 to the third internal space 80 is referred to as a gas distribution part as well.

The gas inlet 10, the buffer space 12, the first internal space 20, the second internal space 40, and the third internal space 80 are interior spaces provided by hollowing out the spacer layer 5. The buffer space 12, the first internal space 20, the second internal space 40, and the third internal space 80 are each provided, with its upper portion defined by the lower surface of the second solid electrolyte layer 6, its lower portion defined by the upper surface of the first solid electrolyte layer 4, and its side portion defined by a side surface of the spacer layer 5.

The first diffusion control part 11, the second diffusion control part 30, the fourth diffusion control part 13, and the third diffusion control part 45 are each provided as two horizontally long slits (which are openings longitudinally extending perpendicular to the sheet of FIG. 1).

At a position that is located between an upper surface of the third substrate layer 3 and a lower surface of the spacer layer 5 and is farther from the distal-end side than the gas distribution part, a reference gas introduction space 43 is provided. The reference gas introduction space 43 is an interior space with its upper portion defined by the lower surface of the spacer layer 5, its lower portion defined by the upper surface of the third substrate layer 3, and its side portion defined by a side surface of the first solid electrolyte layer 4. For example, oxygen or air is introduced into the reference gas introduction space 43 as a reference gas.

The gas inlet 10 is a part being open to the outside. Through this gas inlet 10, a measurement gas is taken into the sensor element 101 from the outside.

The first diffusion control part 11 is a part that applies a predetermined diffusion resistance to the measurement gas taken through the gas inlet 10. Alternatively, without the gas inlet 10, the sensor element 101 may be configured such that the end of the first diffusion control part 11 is positioned at the end of the sensor element 101, and the first diffusion control part 11 may serve as the gas inlet 10.

The buffer space 12 is provided to cancel concentration fluctuations of the measurement gas which are caused due to pressure fluctuations of the measurement gas in the outside (in the case where the measurement gas is a vehicle exhaust gas, pulsations of the exhaust gas pressure). The sensor element 101 does not necessarily need to include the buffer space 12.

The fourth diffusion control part 13 is a part that applies a predetermined diffusion resistance to the measurement gas introduced into the first internal space 20 from the buffer space 12. The fourth diffusion control part 13 is a part provided in association with the provision of the buffer space 12.

The first diffusion control part 11 and the first internal space 20 are directly in communication with each other if the buffer space 12 and the fourth diffusion control part 13 are not provided.

The first internal space 20 is provided as a space for adjusting an oxygen partial pressure of the measurement gas introduced through the gas inlet 10. This oxygen partial pressure is adjusted through the operation of a main pumping cell 21.

The main pumping cell 21 is an electrochemical pumping cell (first electrochemical pumping cell) formed of an inside pump electrode 22, an outside pump electrode 23, and the oxygen-ion conductive solid electrolyte sandwiched between these electrodes. The inside pump electrode 22 is provided on substantially the entire upper surface of the first solid electrolyte layer 4, substantially the entire lower surface of the second solid electrolyte layer 6, and substantially the entire side surface of the spacer layer 5, these surfaces defining the first internal space 20. The outside pump electrode 23 is provided so as to be exposed to the outside in the region corresponding to the inside pump electrode 22 on the upper surface of the second solid electrolyte layer 6. The inside pump electrode 22 and the outside pump electrode 23 are each formed as a porous cermet electrode rectangular in plan view (for example, a cermet electrode made of $ZrO_2$ and a precious metal such as Pt containing 0.1 wt % to 30.0 wt % Au). The inside pump electrode 22 is formed of a material having a lower ability to reduce a NO component of the measurement gas or having no reducing ability. In other words, the inside pump electrode 22 is formed as a low-NO-reducing pump electrode having a limited ability to reduce a NO component.

The main pumping cell 21 causes, upon application of a pump voltage Vp0 by a variable power source 24 provided outside the sensor element 101, a pump current Ip0 to flow between the outside pump electrode 23 and the inside pump electrode 22 in the positive direction or the negative direction, allowing oxygen in the first internal space 20 to be pumped out to the outside or outside oxygen to be pumped into the first internal space 20.

In the sensor element 101, the inside pump electrode 22, a reference electrode 42 sandwiched between the upper surface of the third substrate layer 3 and the first solid electrolyte layer 4, and the oxygen-ion conductive solid electrolyte sandwiched between these electrodes constitute a first oxygen-partial-pressure detection sensor cell 60 being an electrochemical sensor cell. The reference electrode 42 is an electrode substantially rectangular in plan view, which is formed of a porous cermet similar to, for example, the outside pump electrode. Provided around the reference electrode 42 is a reference gas introduction layer 48 that is made of porous alumina and is continuous with the reference gas introduction space 43, so that the reference gas of the reference gas introduction space 43 is introduced to the surface of the reference electrode 42. In the first oxygen-partial-pressure detection sensor cell 60, an electromotive force V0 is generated between the inside pump electrode 22 and the reference electrode 42, which results from an oxygen concentration difference between the atmosphere in the first internal space 20 and the reference gas of the reference gas introduction space 43.

The electromotive force V0 generated in the first oxygen-partial-pressure detection sensor cell 60 varies in accordance with the oxygen partial pressure in the atmosphere present in the first internal space 20. The sensor element 101 uses this electromotive force V0 to feedback-control the variable power source 24 for the main pumping cell 21. This allows the pump voltage Vp0, which is applied to the main pumping cell 21 by the variable power source 24, to be controlled in accordance with the oxygen partial pressure in the atmosphere of the first internal space 20. The sensor element 101 according to this embodiment controls the pump voltage Vp0 to be applied to the main pumping cell 21 by the variable power source 24 such that the oxygen partial pressure in the atmosphere of the first internal space 20 has a predetermined value sufficiently low enough to control an oxygen partial pressure in the second internal space 40.

The second diffusion control part 30 is a part that applies a predetermined diffusion resistance to the measurement gas introduced into the second internal space 40 from the first internal space 20.

The second internal space 40 is provided as a space for performing the process for causing an inflammable gas component of the measurement gas introduced through the second diffusion control part 30 to contain only a hydrocarbon gas.

An auxiliary pumping cell 50 is an auxiliary electrochemical pumping cell (second electrochemical pumping cell) formed of an auxiliary pump electrode 51, the outside pump electrode 23, and the oxygen-ion conductive solid electrolyte sandwiched between these electrodes. The auxiliary pump electrode 51 is provided on substantially the entire upper surface of the first solid electrolyte layer 4, substantially the entire lower surface of the second solid electrolyte layer 6, and substantially the entire side surface of the spacer layer 5, the surfaces defining the second internal space 40. The auxiliary pump electrode 51 is formed as a porous cermet electrode rectangular in plan view, similarly to the outside pump electrode 23 and the inside pump electrode 22. The use of the outside pump electrode 23 is not necessarily required, and another cermet electrode provided on the outer surface of the sensor element 101 may form an outside pump electrode of the auxiliary pumping cell 50, in place of the outside pump electrode 23.

The auxiliary pumping cell 50 causes, upon application of a pump voltage Vp1 by a variable power source 52 provided outside the sensor element 101, a pump current Ip1 to flow between the outside pump electrode 23 and the auxiliary pump electrode 51 in the positive direction, so that oxygen can be pumped out of the second internal space 40.

In the sensor element 101, the auxiliary pump electrode 51, the reference electrode 42, and the oxygen-ion conductive solid electrolyte sandwiched between these electrodes constitute a second oxygen-partial-pressure detection sensor cell 61 being an electrochemical sensor cell. In the second oxygen-partial-pressure detection sensor cell 61, an electromotive force V1 is generated between the auxiliary pump electrode 51 and the reference electrode 42, which results from an oxygen concentration difference between the atmosphere in the second internal space 40 and the reference gas (air) of the reference gas introduction space 43.

The electromotive force V1 to be generated in the second oxygen-partial-pressure detection sensor cell 61 varies in accordance with the oxygen partial pressure in the atmosphere present in the second internal space 40. The sensor element 101 uses this electromotive force V1 to feedback-control the variable power source 52 for the auxiliary pumping cell 50. This allows the pump voltage Vp1, which is applied to the auxiliary pumping cell 50 by the variable power source 52, to be controlled in accordance with the oxygen partial pressure in the atmosphere present in the second internal space 40. The sensor element 101 according to this embodiment controls the pump voltage Vp1 applied to the auxiliary pumping cell 50 by the variable power source 52 such that the oxygen partial pressure in the atmosphere of the second internal space 40 has a predetermined value sufficiently low enough to have substantially no influence on the measurement of the NOx concentration.

The third diffusion control part 45 is a part that applies a predetermined diffusion resistance to the measurement gas introduced into the third internal space 80 from the second internal space 40.

The third internal space 80 is provided as a space for performing the process for measuring the concentration of a NOx gas in the measurement gas introduced through the third diffusion control part 45. The sensor element 101 can pump out oxygen present in the third internal space 80 through the operation of a measuring pumping cell 47. The measuring pumping cell 47 is an electrochemical pumping cell (measuring pumping cell) including the outside pump electrode 23, a measuring electrode 44, and the oxygen-ion conductive solid electrolyte sandwiched between these electrodes.

The measuring electrode 44 is a porous cermet electrode substantially rectangular in plan view, which is included in the third internal space 80. The measuring electrode 44 is formed of a metal capable of reducing a NOx gas and a porous cermet made of zirconia. Pt, which is a main component, containing Rh can be used as a metal component. This causes the measuring electrode 44 to also function as a NOx reducing catalyst that reduces NOx present in the atmosphere of the third internal space 80. The measuring electrode 44 generates oxygen through the reduction or decomposition of NOx of the measurement gas by catalytic activation.

The sensor element 101 includes a measuring sensor cell 41. The measuring sensor cell 41 is an electrochemical sensor cell composed of the measuring electrode 44, the reference electrode 42, and the oxygen-ion conductive solid electrolyte sandwiched between these electrodes. The measuring sensor cell 41 generates an electromotive force V2 between the measuring electrode 44 and the reference electrode 42 in accordance with the oxygen concentration difference between the atmosphere of the third internal space 80 (in particular, the atmosphere in the vicinity of the surface of the measuring electrode 44) and the reference gas of the reference gas introduction space 43. The sensor element 101 uses this electromotive force V2 to feedback-control the variable power source 46 for the measuring pumping cell 47 provided outside the sensor element 101. This allows the pump voltage Vp2, which is applied to the measuring pumping cell 47 by the variable power source 46, to be controlled in accordance with the oxygen partial pressure in the atmosphere of the third internal space 80.

The measurement gas reaches the third internal space 80 after oxygen is pumped out of the first internal space 20 and the second internal space 40. It means that oxygen, which is present in the atmosphere of the third internal space 80, is generated through the decomposition of NOx in the measuring electrode 44. Thus, the current (NOx current) Ip2 flowing through the measuring pumping cell 47 is substantially proportional to the NOx concentration of the measurement gas (the NOx current Ip2 and the NOx concentration are in a linear relationship). The sensor element 101 detects such a NOx current Ip2 and obtains the NOx concentration of the measurement gas based on the pre-identified functional relationship (linear relationship) between the NOx current Ip2 and the NOx concentration.

The sensor element 101 is configured to measure an electromotive force $V_{ref}$ generated between the outside pump electrode 23 and the reference electrode 42 to obtain the oxygen partial pressure outside the sensor element 101.

In the sensor element 101, further, a heater 70 is formed to be vertically sandwiched between the second substrate layer 2 and the third substrate layer 3. The heater 70 generates heat by power feeding from the outside through a heater electrode (not shown) provided on the lower surface of the first substrate layer 1. Heat generation by the heater 70 increases the oxygen-ion conductivity of the solid electrolyte forming the sensor element 101. The heater 70 is buried over the entire area extending from the first internal space 20 to the second internal space 40 to heat a predetermined portion of the sensor element 101 to a predetermined temperature or maintain the temperature of the predetermined portion at a predetermined temperature. Formed on the upper and lower surfaces of the heater 70 is a heater insulating layer 72 made of, for example, alumina to obtain electrical insulation between the heater 70 and the second substrate layer 2 and the third substrate layer 3 (hereinafter, the heater 70, the heater electrode, and the heater insulating layer 72 are correctively referred to as a heater part as well).

<Setting of Temperature Rising Profile when Use of Gas Sensor is Initiated>

The following describes how a temperature rising profile is set, which is used when the temperature of the sensor element 101 is increased to a predetermined operating temperature (for example, 700° C. to 900° C.) by the heater 70 in initiating the use of the gas sensor 100 according to this embodiment. In this embodiment, a temperature rising profile is set in such a range that causes no crack in the sensor element 101.

Figure 2:
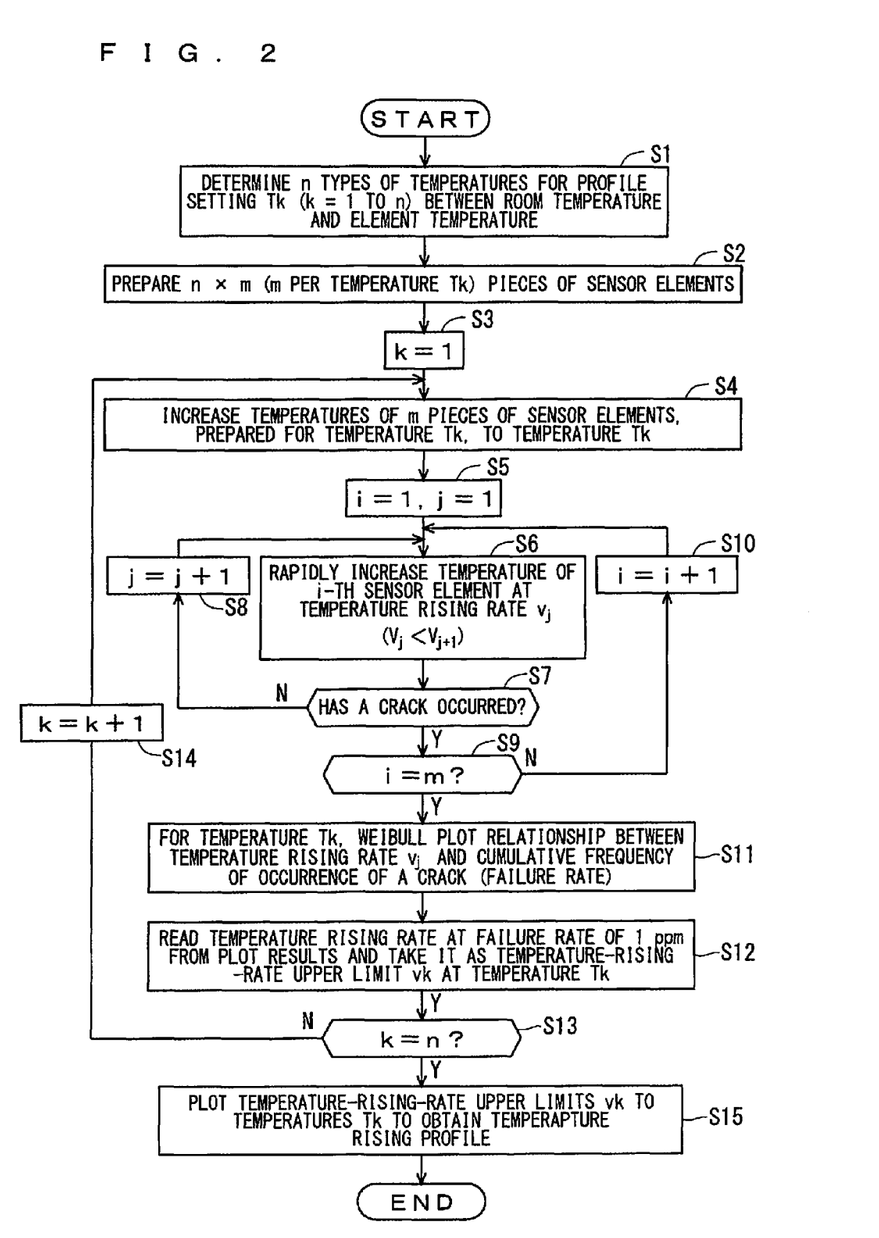
FIG. 2 shows the procedure of setting a temperature rising profile.

FIG. 2 shows the procedure of setting such a temperature rising profile.

First, a plurality of temperatures for profile setting Tk (k is a natural number from 1 to n) are determined at appropriate temperature intervals such that temperature becomes higher with a larger value of k (Step S1). Although the temperatures for profile setting always need not to be determined at equal temperature intervals, at least a temperature Tn, which is an upper limit temperature for profile setting where k=n, is preferably set to be equal to the operating temperature of the sensor element 101 or set to be in the range up to about 100° C. higher than the operating temperature. The following describes an example in which the operating temperature of the sensor element 101 is 830° C., T1=120° C., T2=320° C., T3=520° C., T4=710° C., and T5=890° C.

Then, m pieces of sensor elements 101 per temperature for profile setting Tk, that is, n×m=nm pieces of sensor elements 101 are prepared (Step S2).

Subsequently, in the case of k=1 (Step S3), the temperatures of the m sensor elements 101 applied for the temperature for profile setting Tk are increased to the temperature Tk by the heater 70 (Step S4). The temperature rising rate in this case is a value at which the occurrence of no crack in the sensor element 101 has been empirically confirmed. The temperature rising rate when the heater 70 increases the temperature of the sensor element 101 is controllable by adjusting the voltage applied to the heater 70. The actual temperature of the sensor element 101 can be obtained, for example, with a radiation thermometer or from a heater resistance value.

Then, the temperature of the sensor element 101 is stabilized at a temperature for profile setting T1, and subsequently, in the cases of i=1 and j=1 (Step S5), the temperature of an i-th sensor element 101 is increased rapidly by the heater 70 at a temperature rising rate $v_j$ (Step S6). Herein, i is a natural number from one to m, and j is a natural number equal to one or more. The temperature rising rate $v_j$ is a change rate of temperature to time, which is also represented as $v_j=(dT/dt)_j$.

Figure 3:
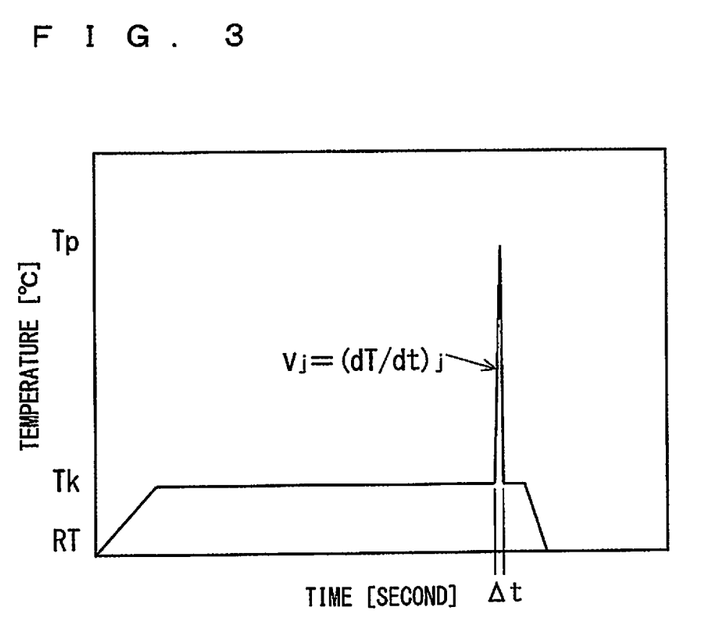
FIG. 3 schematically shows a set temperature profile in Steps S4 and S6.

FIG. 3 schematically shows the set temperature profile in Steps S4 and S6. This set temperature profile is equivalent to a profile in which the vertical axis of the profile of the voltage applied to the heater 70 is replaced with temperature.

First, in Step S4, the temperature of the sensor element 101 is increased from room temperature to the temperature for profile setting Tk at a predetermined rate, and subsequently, the sensor element 101 is maintained at the temperature Tk for a predetermined time period. In Step S6, then, the temperature of the sensor element 101 is rapidly increased at a temperature rising rate After the rapid temperature rising, the temperature of the sensor element 101 is immediately decreased to the original temperature Tk. More specifically, as shown in FIG. 3, a rapid temperature rising is performed by application of a triangle wave during a time period Δt. FIG. 3 shows, as Tp, a maximum achieving temperature during the time period Δt after the start of the rapid temperature rising.

Then, whether a crack has occurred in the sensor element 101 as a result of the rapid temperature rising is checked visually, for example (Step S7).

If no crack has occurred in the sensor element 101 as a result of the rapid temperature rising (NO in Step S7), j=j+1 (Step S8), and the procedure returns to Step S6 to rapidly increase the temperature of the same sensor element 101 at a temperature rising rate $v_{j+1}$ greater than the temperature rising rate $v_j$. In other words, this is the process of repeatedly performing a temperature rising while increasing a temperature rising rate until a crack occurs in the sensor element 101.

If a crack has occurred in the sensor element 101 as a result of the rapid temperature rising (YES in Step S7), and if i≠m, that is, if the sensor element 101 that has not been subjected to the rapid temperature rising is left (NO in Step S9), i=i+1 (Step S10), and Steps S6 and S7 are repeated on an (i+1)th sensor element 101.

Steps S6 and S7 may be simultaneously performed on the m pieces of sensor elements 101.

If i=m, that is, if a crack has occurred in all the sensor elements 101 after the rapid temperature rising (YES in Step S9), the relationship between the temperature rising rate $v_j$ and the cumulative frequency of the occurrence of a crack (failure rate) is Weibull plotted for the temperature for profile setting Tk (Step S11).

Figure 4:
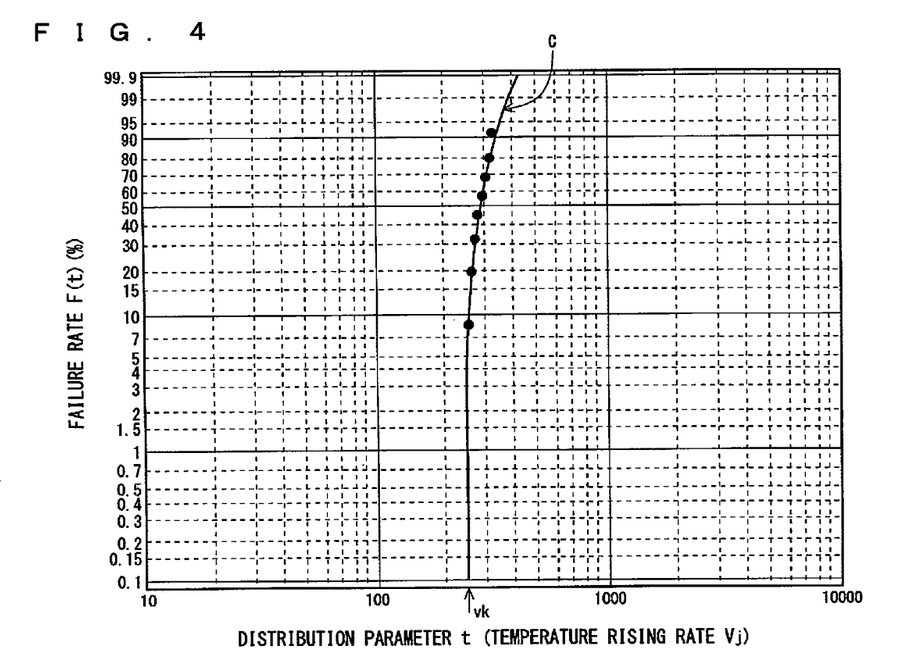
FIG. 4 shows Weibull plot results of a failure rate F(t), where a temperature rising rate $v_j$ is a distribution parameter t.

FIG. 4 shows the Weibull plot results with a failure rate F(t), where the temperature rising rate $v_j$ is a distribution parameter t. FIG. 4 illustrates a case of m=8, where black circles indicate the plot results for eight (i=1 to 8) sensor elements 101.

After the Weibull plot is obtained, a temperature rising rate $v_j$ when the failure rate F(t) is 1 ppm=0.0001% is estimated from the plot results, and a value thereof is set as a temperature-rising-rate upper limit vk at the temperature for profile setting Tk (Step S12).

Specifically, an approximate curve C as shown in FIG. 4 is drawn, and an extrapolation point thereof is taken as a temperature-rising-rate upper limit vk by reading a temperature rising rate $v_j$ when the failure rate F(t) is 1 ppm. Known techniques such as the least squares method are applicable to the setting the approximate curve C. In the case shown in FIG. 4, the approximate curve C is almost linear at failure rates F(t) of 1% or less.

If there is a temperature for profile setting Tk where k≠n, that is, a temperature-rising-rate upper limit vk is not determined (NO in Step S13), setting is made such that k=k+1 (Step S14), and then, Steps S4 to S12 are repeated. In other words, a temperature-rising-rate upper limit vk is determined for all the temperatures for profile setting Tk.

If k=n, that is, a temperature-rising-rate upper limit vk is determined for all the temperatures for profile setting Tk (YES in Step S13), those n temperature-rising-rate upper limits vk (v1 to v5) are plotted against the temperatures for profile setting Tk and then, based on these plotting results, a temperature rising profile when the use of the gas sensor 100 is initiated is obtained (Step S15).

Figure 5:
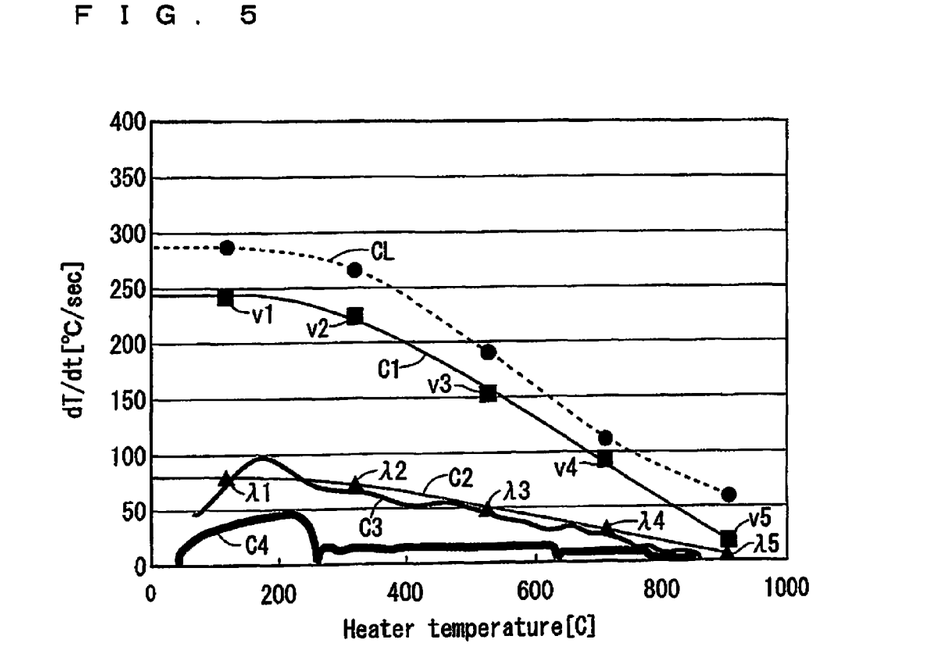
FIG. 5 shows the results obtained by plotting temperature-rising-rate upper limits vk against temperatures for profile setting Tk (T1 to T5)

FIG. 5 shows the results obtained by plotting the temperature-rising-rate upper limits vk (v1 to v5) against the temperatures for profile setting Tk (T1 to T5). FIG. 5 shows data points individually indicating the temperature-rising-rate upper limits v1 to v5 by black squares and also shows a temperature-rise upper limit curve C1 being an approximate curve on the data points. The temperature-rise upper limit curve C1 can be set by a known technique, for example, the least squares method. The temperature-rise upper limit curve C1 indicates an upper limit of the temperature rising rates that can be obtained while the sensor element 101 is heated to the temperature (heater temperature) indicated by the horizontal axis. Additionally, FIG. 5 shows average values of the temperature rising rates $v_j$ at which a crack has occurred in the eight (i=1 to 8) sensor elements 101 individually for the temperatures T1 to T5 and also schematically shows a curve CL passing through the average values, where the curve CL corresponds to a crack limit at which a crack is highly likely to occur.

The results shown in FIG. 5 reveal that to increase the temperature of the sensor element 101 without causing a crack, the temperature rising rate needs to be made smaller as temperature is increased to higher temperature. The results, meanwhile, suggest that the temperature rising rate may be relatively large at lower temperatures. The above is effective to reduce a light-off time because although, to reduce a light-off time, oxygen needs to be discharged from the third internal space 80, in which the measuring electrode 44 is included, by the measuring pumping cell 47 as soon as possible, after the activation of the gas sensor 100, the measuring pumping cell 47 cannot be operated unless the temperature of the sensor element 101 rises to some extent and a resistance value is stabilized.

By determining a temperature rising profile such that a temperature rising rate changes along the temperature-rise upper limit curve C1, in theory, a temperature rising is enabled in a sufficiently small failure rate range also at temperatures other than the temperature for profile setting Tk.

However, an actual temperature rising of the sensor element 101 may involve a non-uniform temperature, a delay in response time, or an overshoot due to location. This may cause a temperature rising at a temperature rising rate equal to or higher than the crack limit during temperature rise, even though it is temporarily.

From the viewpoint of more reliably preventing or reducing the occurrence of a crack, a temperature rising profile is more preferably determined by taking into account a certain safety rate than by determining a temperature rising profile using the temperature-rise upper limit curve C1 per se.

Such a temperature rising profile can be set in various manners. The following describes, as an example manner, the case where λk=vk/3, which is a value obtained by dividing the temperature-rising-rate upper limit vk of each temperature for profile setting Tk by three, is used as a reference (reference rate) in setting a temperature rising profile. It is not essential to take a value obtained by dividing the temperature-rising-rate upper limit vk by three as a reference rate λk, and alternatively, a value obtained by dividing the temperature-rising-rate upper limit vk by another value (which may not be an integer) may be used.

In this case, specifically as shown in FIG. 5, the respective data points indicating reference rates λk for the temperatures for profile setting T1 to T5 are plotted as black triangles, and a setting reference curve C2 being an approximate curve for those data points is obtained, to thereby determine a temperature rising profile based on the setting reference curve C2. As in the case of the temperature-rise upper limit curve C1, a known technique is applicable to setting the setting reference curve C2.

Figure 6:
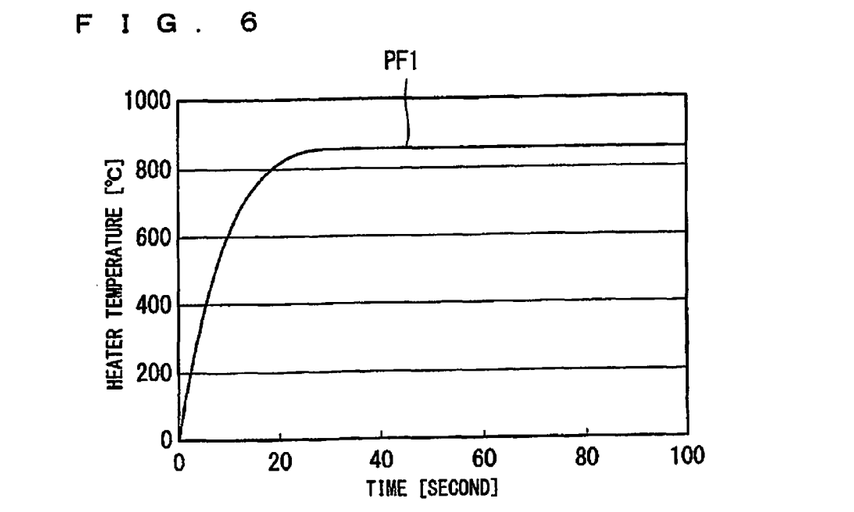
FIG. 6 shows a temperature rising profile PF1, with a temperature rising rate determined to precisely follow a setting reference curve C2 shown in FIG. 5.

FIG. 6 shows a temperature rising profile PF1 in which a temperature rising rate is determined so as to closely follow the setting reference curve C2 shown in FIG. 5. In other words, the temperature rising profile PF1 satisfies such a condition that for an appropriate temperature, a temperature rising rate at this appropriate temperature has a value on the setting reference curve C2. As shown in FIG. 6, the temperature rising profile PF1 is obtained as a curve (function) that is convex upward in which an initial temperature rising rate is the largest temperature rising rate and thereafter the temperature rising rate gradually decreases. Also, the temperature rising profile is not required to be a curve (function) that is convex upward and may be, for example, an appropriate curve (function) that is convex downward. The temperature rising profile PF1 of FIG. 6 shows that in initiating the use of the gas sensor 100, the temperature of the sensor element 101 can be increased up to 830° C. being an operating temperature within 30 seconds after the temperature of the heater 70 of the sensor element 101 is increased through energization.

Once the above-mentioned temperature rising profile PF1 is created, through a temperature rising using such a temperature rising profile PF1, the sensor element 101 produced in the same process can be quickly heated to the operating temperature without any crack.

In the case of a temperature rising based on the temperature rising profile PF1 shown in FIG. 6, however, a temperature change until the element temperature is reached is curvilinear, and accordingly, a temperature rising rate being a rate of change in temperature needs to be changed continuously, resulting in complicated control. Meanwhile, the actual temperature rising of the sensor element 101 does not always closely follow the set temperature rising profile, and a time delay or overshoot may occur transiently. Thus, it has also been confirmed that substantially identical effects are achieved even if not-so-complicated control is performed and a profile is simplified within a certain range.

Figure 7:
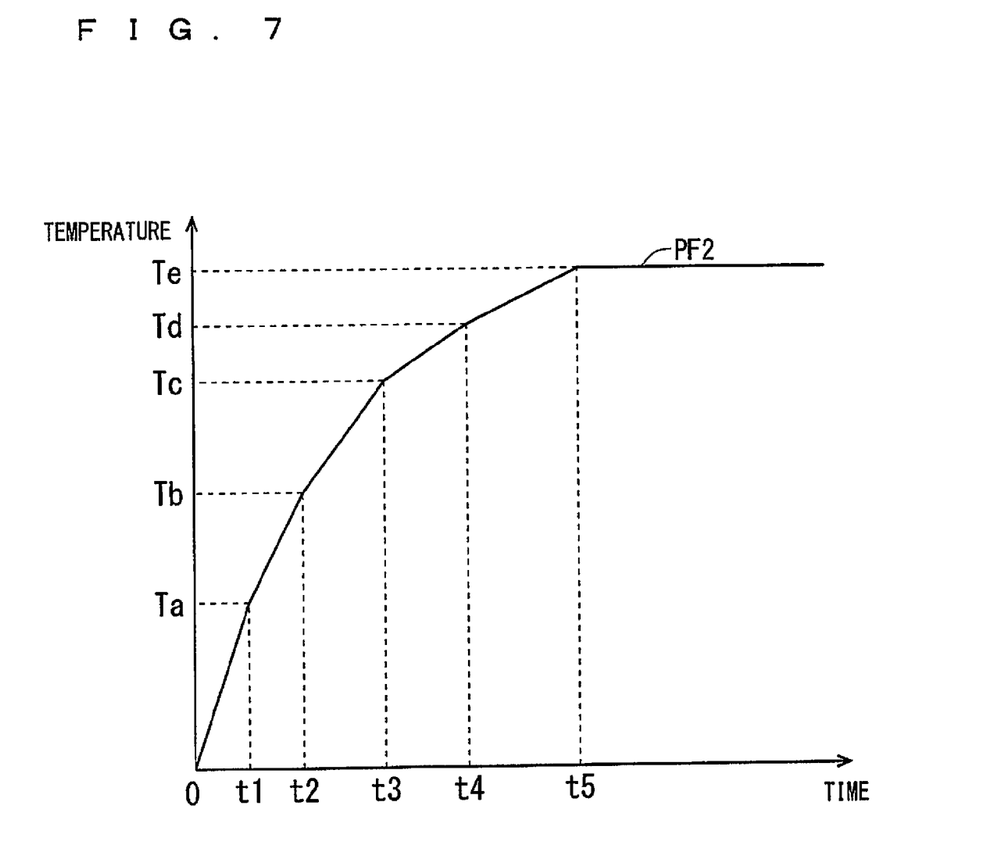
FIG. 7 schematically shows a temperature rising profile PF2.

For example, FIG. 7 schematically shows a temperature rising profile PF2 that reflects the above-mentioned points. The temperature rising profile PF2 is obtained by sequentially connecting points at a temperature-rising start temperature, a plurality of control switching temperatures and an operating temperature on the temperature rising profile PF1 in a linear manner. That is, in the temperature rising profile PF2, a range from the temperature-rising start temperature to the operating temperature to be reached is divided into a plurality of stages, and a temperature rising is performed in such a manner (multistage control) that heating until reaching to each control switching temperature is performed at an individual constant temperature rising rate. In other words, such a temperature rising profile PF2 is obtained by temporarily obtaining the temperature rising profile PF1 as a provisional profile, dividing the temperature range from the temperature-rising start temperature to the operating temperature into multiple stages with a plurality of control switching temperatures as boundary values, and setting the slope of an approximate straight line of the provisional profile at each of the multiple stages as a temperature rising rate in each stage.

In the case shown in FIG. 7, five-stage control of switching temperature rising rates is performed at points in time when four control switching temperatures Ta (arrival time t1), Tb (arrival time t2), Tc (arrival time t3), and Td (arrival time t4), and operating temperature Te (arrival time t5) are individually reached after the start of a temperature rising at a time 0. As shown in FIG. 6, in the temperature rising profile PF1, it is usual that an initial temperature rising rate is the largest temperature rising rate and thereafter the temperature rising rate gradually decreases. Thus, also in the temperature rising profile PF2 for multistage control, based on the temperature rising profile PF1, an initial temperature rising rate is the largest temperature rising rate and thereafter the temperature rising rate gradually decreases.

The setting number of control switching temperatures (the number of control stages), including an operating temperature, is preferably four or more and is more preferably five or more. The number of control stages equal to or less than three is not preferable because the divergence from the temperature rising profile PF1 becomes large.

Although the upper limit of the number of control stages is not especially limited, in practice, the upper limit is preferably in the range not exceeding ten stages because multistate control having a larger number of control stages approaches the temperature rising profile PF1 and an advantage of multistage control, in which a temperature rising profile is more simplified, is lost.

Figure 8:
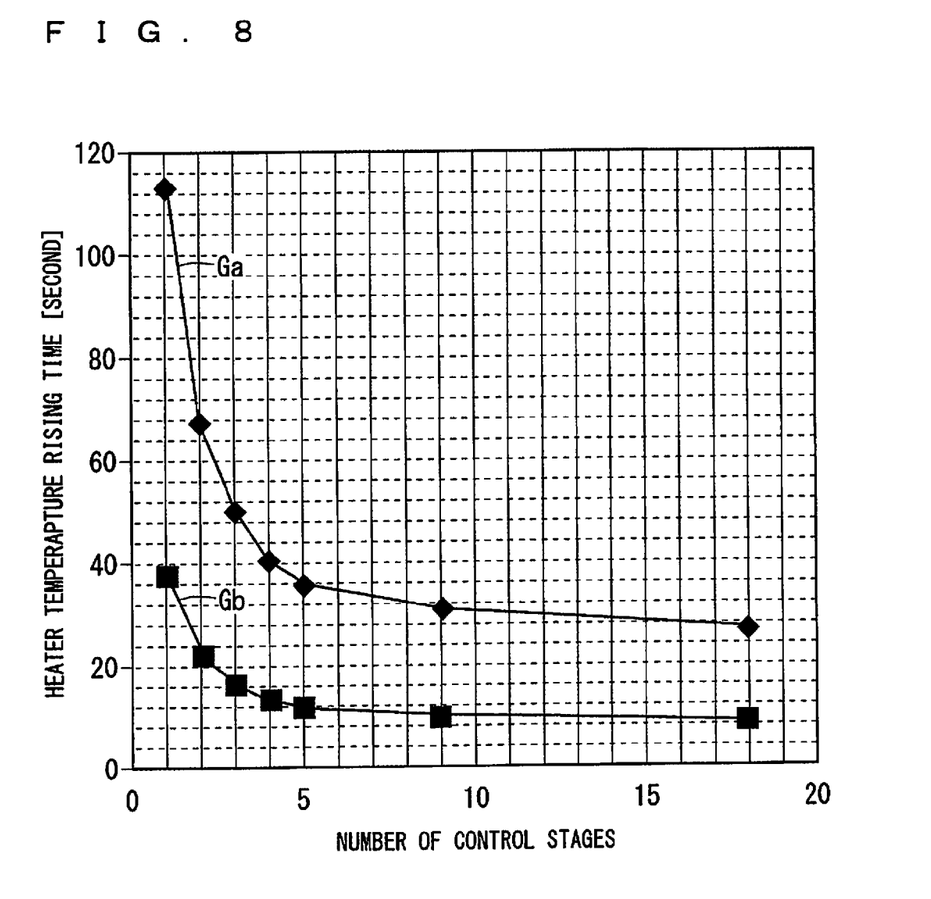
FIG. 8 shows the relationship between the number of control stages and a temperature rising time.

FIG. 8 shows the relationship between the number of control stages and a temperature rising time to describe the above-mentioned points.

In FIG. 8, a graph Ga shows the times required for the sensor element 101 to reach the operating temperature 830° C. when the number of control stages is varied from one to 18 based on the temperature rising profile PF1. The case where the number of control stages is one corresponds to the case where the temperature of the sensor element 101 is increased from the start at a constant temperature rising rate. Specifically, this is the case where a temperature rising is performed at a temperature rising rate which is a value at 830° C. of the setting reference curve C2 shown in FIG. 5. In the case where the number of control stages is plural, the last control switching temperature is an operating temperature, and the control switching temperatures in between are set at substantially identical temperature intervals.

A graph Gb shows the results when a temperature rising profile similar to the temperature rising profile PF1 shown in FIG. 6 is created based on the temperature-rise upper limit curve C1 shown in FIG. 5, where the number of control stages is varied based on the created profile.

The graph Ga and the graph Gb both show a change in which the temperature rising time decreases with a larger number of control stages, and eventually, becomes saturated. The saturation value of the graph Ga is substantially equal to the time until an operating temperature is reached in the temperature rising profile PF1. Although not described in detail, the saturation value of the graph Gb is substantially equal to a similar time in its corresponding temperature rising profile (not shown).

In the case of the graph Ga, a difference between the temperature rising time and the saturation value is a little over 10 seconds for four control stages, and such a difference is reduced to 10 seconds or less for five or more control stages. In the case of the graph Gb, similarly, a difference between the temperature rising time and the saturation value is reduced to five seconds or less for four or more control stages.

In the graph Ga, further, for four or less control stages, a temperature rising time is substantially equal to or less than the temperature rising time for one control stage in the graph Gb. This means that even in the case where a temperature rising profile is set based on the setting reference curve C2 having a smaller temperature rising rate than that of the temperature-rise upper limit curve C1, the application of multistage control can quickly increase the temperature of the sensor element 101 with a reduced possibility of the occurrence of a crack.

As described above, according to this embodiment, it is possible to quickly increase the temperature of the sensor element while reliably preventing or reducing the occurrence of a crack, by determining a temperature rising profile for increasing the temperature of the sensor element in initiating the use of a gas sensor based on a crack occurrence situation when the temperature of the sensor element is rapidly increased, specifically, by determining a temperature rising profile such that a failure rate when a rapid temperature rising is performed in the temperature range from room temperature to the element operating temperature. This temperature rising profile can set a temperature rising rate to a relatively large value in the low temperature range, achieving an effect of a reduced light-off time.

Moreover, a temperature rising from the temperature-rising start temperature to the operating temperature is performed by multistage control in which heating until reaching to control switching temperatures determined in four to ten stages in advance, including the operating temperature, is performed at an individual constant temperature rising rate, allowing the temperature of the sensor element to rise quickly while reliably preventing or reducing the occurrence of a crack during the use of a temperature rising profile whose control is simplified.

EXAMPLES

Example

FIG. 5 shows, as a curve C3, how the temperature rising rate of the sensor element 101 actually changes for five control stages in the graph Ga of FIG. 8. In other words, the curve C3 indicates how the temperature of the sensor element 101 is actually increased based on the temperature rising profile set in the embodiment above.

It is revealed from the curve C3 that the temperature rising rate changes substantially along the setting reference curve C2, with slight changes. The temperature rising time was 35 seconds, as shown in FIG. 8. The curve C3 fell below the temperature-rise upper limit curve C1, and the occurrence of a crack was not found in the sensor element 101 after a temperature rising. A gap at a lower temperature portion of the curve C3 with the setting reference curve C2 is large because the controller used in the temperature rising unsuccessfully provided a high temperature rising rate in the beginning of the temperature rising.

The results above reveal that the temperature of the sensor element 101 can be actually increased based on the embodiment above.

Comparative Example

As in the technique disclosed in Japanese Patent No. 4344486, the temperature of the sensor element 101 was increased by feedback control based on a heater resistance, using a curve in which a time change of a heater resistance value is approximated to an exponential function (first-order lag function). Four stages of target heater resistances were set. How the temperature rising rate changes in this case is indicated as a curve C4 in FIG. 5.

In such a case, as can be seen from the curve C4, the temperature rising rates at the second and following stages particularly had excellent stability, but temperature rising rates were generally lower than those of the example, and it took 65 seconds to increase temperature to the operating temperature. The occurrence of a crack was not found in the sensor element 101 after the temperature rising.

The results above reveal that a temperature rising is enabled more quickly in the example than in the comparative example.

What is claimed is:

1. A method for setting a temperature rising profile for increasing a temperature of a sensor element formed of an oxygen-ion conductive solid electrolyte, the sensor element being included in a gas sensor and including
   at least one internal space into which a measurement gas is introduced,
   an electrochemical pumping cell formed of a measuring electrode disposed in one of the at least one internal space, a pump electrode disposed in a portion different from the at least one internal space, and the solid electrolyte, and
   a heater for heating the sensor element,
   the gas sensor identifying a concentration of a predetermined gas component of the measurement gas based on a pump current through the electrochemical pumping cell,
   the temperature rising profile indicating a change in an increased temperature set relative to a temperature rising time when the heater increases the temperature of the sensor element in activation of the gas sensor,
   said method comprising:
   repeating a rapid temperature rising by the heater, for each of a plurality of the sensor elements having a temperature increased to a predetermined temperature for profile setting by the heater, while changing a temperature rising rate until a crack occurs;
   Weibull plotting a failure rate that is a cumulative frequency, at which cracks occur in the plurality of sensor elements in the rapid temperature rising, for the predetermined temperature for profile setting using the temperature rising rate as a distribution parameter;
   identifying, as a temperature-rising-rate upper limit, a temperature rising rate at which a failure rate is 1 ppm from the results of the Weibull plotting;
   determining, based on the temperature-rising-rate upper limit for a plurality of temperatures for profile setting, a temperature-rise upper limit curve indicating a change in the temperature-rising-rate upper limit relative to an increased temperature, the plurality of temperatures for profile setting differing from each other and including a temperature equal to or higher than an operating temperature of the sensor element; and
   determining, as an appropriate function, the temperature rising profile in a range in which a temperature rising rate at an appropriate temperature does not exceed values on the temperature-rising-rate upper limit curve for the temperature.

2. The method for setting a temperature rising profile of a sensor element according to claim 1, wherein in said determining the temperature rising profile, the temperature rising profile is determined as a function that is convex upward in a range in which a temperature rising rate at an appropriate temperature does not exceed values on the temperature-rising-rate upper limit curve.

3. The method for setting a temperature rising profile of a sensor element according to claim 1, wherein said determining the temperature rising profile, includes
   determining a temperature-rising-rate reference curve indicating a change in a temperature rising rate relative to an increased temperature in a range in which a temperature rising rate at an appropriate temperature does not exceed values on the temperature-rising-rate upper limit curve,
   setting a provisional temperature rising profile in which a temperature rising rate follows the temperature-rising-rate reference curve,
   setting a plurality of control switching temperatures, with the operating temperature of the sensor element being a maximum value,
   dividing a temperature range from a temperature-rising start temperature being a temperature of the sensor element in the activation of the gas sensor to the operating temperature into a plurality of stages, each of the plurality of control switching temperatures being a boundary value, and setting a slope of an approximate straight line of the provisional profile at each of the plurality of stages as the temperature rising rate at each stage to obtain the temperature rising profile.

4. The method for setting a temperature rising profile of a sensor element according to claim 3, wherein the plurality of stages comprise four or more stages.

5. The method for setting a temperature rising profile of a sensor element according to claim 4, wherein the plurality of stages comprise four to ten stages.

6. The method for setting a temperature rising profile of a sensor element according to claim 5, wherein the plurality of stages comprise five or more stages and ten or less stages.

7. The method for setting a temperature rising profile of a sensor element according to claim 3, wherein in said determining a temperature-rising-rate reference curve, the reference curve is determined to pass through a value that is one-third of a temperature-rising-rate upper limit of the plurality of temperatures for profile setting.

8. The method for setting a temperature rising profile of a sensor element according to claim 1, wherein said determining the temperature rising profile includes
    determining a temperature-rising-rate reference curve indicating a change in a temperature rising rate relative to an increased temperature in a range in which a temperature rising rate at an appropriate temperature does not exceed values on said temperature-rising-rate upper limit curve, and
    setting a temperature rising profile such that a temperature rising rate follows said temperature-rising-rate reference curve.

9. The method for setting a temperature rising profile of a sensor element according to claim 1, wherein
    the sensor element includes as the at least one internal space,
        a first internal space in communication with the outside under a predetermined diffusion resistance,
        a second internal space in communication with the first internal space under a predetermined diffusion resistance, and
        a third internal space in communication with the second internal space under a predetermined diffusion resistance, and
    the measuring electrode is disposed in the third internal space.

10. The method for setting a temperature rising profile of a sensor element according to claim 2, wherein said determining the temperature rising profile includes
    determining a temperature-rising-rate reference curve indicating a change in a temperature rising rate relative to an increased temperature in a range in which a temperature rising rate at an appropriate temperature does not exceed values on the temperature-rising-rate upper limit curve,
    setting a provisional temperature rising profile in which a temperature rising rate follows the temperature-rising-rate reference curve,
    setting a plurality of control switching temperatures, with the operating temperature of the sensor element being a maximum value,
    dividing a temperature range from a temperature-rising start temperature being a temperature of the sensor element in the activation of the gas sensor to the operating temperature into a plurality of stages, each of the plurality of control switching temperatures being a boundary value, and
    setting a slope of an approximate straight line of the provisional profile at each of the plurality of stages as the temperature rising rate at each stage to obtain the temperature rising profile.

11. The method for setting a temperature rising profile of a sensor element according to claim 10, wherein the plurality of stages comprise four or more stages.

12. The method for setting a temperature rising profile of a sensor element according to claim 11, wherein the plurality of stages comprise four to ten stages.

13. The method for setting a temperature rising profile of a sensor element according to claim 12, wherein the plurality of stages comprise five or more stages and ten or less stages.

14. The method for setting a temperature rising profile of a sensor element according to claim 10, wherein in said step of determining the temperature-rising-rate reference curve, said reference curve is determined to pass through a value that is one-third of a temperature-rising-rate upper limit of said plurality of temperatures for profile setting.

15. The method for setting a temperature rising profile of a sensor element according to claim 2, wherein said determining a temperature-rising-rate reference curve includes
    determining a temperature-rising-rate reference curve indicating a change in a temperature rising rate relative to an increased temperature in a range in which a temperature rising rate at an appropriate temperature does not exceed values on the temperature-rising-rate upper limit curve, and
    setting a temperature rising profile such that a temperature rising rate follows the temperature-rising-rate reference curve.

16. The method for setting a temperature rising profile of a sensor element according to claim 2, wherein
    the sensor element includes as the at least one internal space,
        a first internal space being in communication with the outside under a predetermined diffusion resistance,
        a second internal space being in communication with the first internal space under a predetermined diffusion resistance, and
        a third internal space being in communication with the second internal space under a predetermined diffusion resistance,
    the measuring electrode is disposed in the third internal space.

17. The method for setting a temperature rising profile of a sensor element according to claim 3, wherein
    the sensor element includes as the at least one internal space,
        a first internal space being in communication with the outside under a predetermined diffusion resistance,
        a second internal space being in communication with the first internal space under a predetermined diffusion resistance, and
        a third internal space being in communication with the second internal space under a predetermined diffusion resistance, and
    the measuring electrode is provided in the third internal space.

18. The method for setting a temperature rising profile of a sensor element according to claim 7, wherein
    the sensor element includes as the at least one internal space,
        a first internal space being in communication with the outside under a predetermined diffusion resistance, a second internal space being in communication with the first internal space under a predetermined diffusion resistance, and a third internal space being in communication with the second internal space under a predetermined diffusion resistance, and the measuring electrode is provided in the third internal space.

19. The method for setting a temperature rising profile of a sensor element according to claim 8, wherein the sensor element includes as the at least one internal space, a first internal space being in communication with the outside under a predetermined diffusion resistance, a second internal space being in communication with the first internal space under a predetermined diffusion resistance, and a third internal space being in communication with the second internal space under a predetermined diffusion resistance, and the measuring electrode is provided in the third internal space.

20. The method for setting a temperature rising profile of a sensor element according to claim 10, wherein the sensor element includes as the at least one internal space, a first internal space being in communication with the outside under a predetermined diffusion resistance, a second internal space being in communication with the first internal space under a predetermined diffusion resistance, and a third internal space being in communication with the second internal space under a predetermined diffusion resistance, and the measuring electrode is provided in the third internal space.

* * * * *